United States Patent [19]

Juda et al.

[11] Patent Number: 4,844,899
[45] Date of Patent: Jul. 4, 1989

[54] HALOPHOR COMPOSITION

[75] Inventors: Robert H. Juda, Akron, Ohio; Paritosh M. Chakrabarti, Pittsburgh, Pa.; Roger A. Crawford, Wadsworth, Ohio

[73] Assignee: PPG Industries, Inc., Pittsburgh, Pa.

[21] Appl. No.: 819,452

[22] Filed: Jan. 16, 1986

[51] Int. Cl.⁴ ............................................. A01N 59/12
[52] U.S. Cl. .................................. 424/664; 424/677; 424/672; 424/682; 424/670; 424/671; 424/669; 424/678; 424/679; 424/680; 424/681; 424/723; 424/722
[58] Field of Search ........................................ 424/150

[56] References Cited

U.S. PATENT DOCUMENTS 4,131,556 12/1978 Klopolek et al. .................... 424/150

FOREIGN PATENT DOCUMENTS 2525685 12/1976 Fed. Rep. of Germany ...... 424/150
2537 of 1889 United Kingdom ................ 424/150

OTHER PUBLICATIONS

Reactions in Sulfolane II; "Electrochemical Study of Halogen Oxydo–Reducer Systems," R. L. Benoit et al, Canadian Journal of Chemistry, 46, 1261–1266 (1968), (translation).

Primary Examiner—Allen J. Robinson
Attorney, Agent, or Firm—Irwin M. Stein

[57] ABSTRACT

Halophors, e.g., bromophors, comprising a complex of sulfone, e.g., sulfolane, halide ion, e.g., sodium bromide, and halogen, e.g., bromine, are described. Solid, free-flowing halophor compositions of the aforesaid complex and an amorphous siliceous carrier are also described.

25 Claims, No Drawings

HALOPHOR COMPOSITION

DESCRIPTION OF THE INVENTION

The present invention relates to iodine- and/or bromine-containing compositions. More particularly this invention relates to complexes of bromine and/or iodine, halide ion and sulfones, e.g., dimethylsulfone and tetrahydrothiophene-1,1-dioxide (sulfolane), and the use of such compositions as fumigants and sanitizers. The present invention further relates to solid, free-flowing biocide compositions of particulate amorphous siliceous carrier having said iodine and/or bromine compositions adsorbed thereon.

The halogens, i.e., chlorine, bromine, and iodine, are recognized as excellent biocidal materials and are used extensively, particularly in the food processing and handling industries, to prevent bacteriological contamination of foodstuffs. Halogen sanitizers are also used in controlling potentially harmful organisms in potable water, swimming pools, hospitals and wherever harmful organisms can present a contamination problem.

In order to utilize the sanitizing property of bromine or iodine and to eliminate or minimize many of the difficulties involved with their use, complexes of bromine or iodine with various materials, such as surfactants, have been suggested. These bromine-containing complexes have been referred to as "bromophors". The iodine-containing complexes are referred to as "iodophors". The disinfecting and germicidal activity of such "halophors" is derived essentially from the free halogen which the halophors liberate.

Surfactants used to prepare such halophors have been selected from a wide variety of anionic, nonionic and cationic materials. See, for example, British patent specification No. 1,357,365. A further British patent specification No., i.e., 1,237,911, describes disinfectant compositions comprising a mixture of iodine, an ampholytic organo-amino sulfonate, a nonionic surface active agent and a glycol. This composition is described as being adsorbed onto a silica and mixed with animal feed for controlling the growth of microorganisms within animals such as chickens, turkeys, and pigs. The disinfectant compositions described in British patent specification No. 1,237,911 are not typical iodophors, i.e., materials that liberate iodine and which exhibit the conventional starch-iodine reaction. The described compositions do not lose iodine even from boiling aqueous solutions but nevertheless are described as having disinfectant or anti-microbial activity, e.g., for in vivo applications.

Fumigation of grain, fruit, vegetables or other food product commodities stored in bulk with bromine compounds such as methyl bromide, ethylene dibromide, and ethylene chlorobromide is performed by applying the bromine compound to the stored commodity in an enclosure which is as gas tight as possible. Low-boiling bromine-containing fumigants, such as methyl bromide, are piped into the enclosure from cylinders of compressed or liquified gas whereas bromine-containing fumigants boiling at temperatures above ambient are sprayed into the area to be treated, e.g., on top of the stored commodity. Preferably the later type fumigant has a specific gravity greater than air and permeates the stored commodity as it falls to the floor of the enclosure.

The present invention provides halophors and halophor compositions which supply a source of bromine and/or iodine. The halophor compositions can be utilized for biocidal, e.g., sanitizing and disinfecting, applications. In those applications, the halophor is commonly added to the aqueous media used to cleanse the surfaces to be cleaned, whereby the halophor releases halogen which forms hypohalite ion in the aqueous medium, which hypohalite serves as the biocidal agent. More particularly, the bromophor compositions may be used as fumigants for grains, vegetables, fruits, seeds and other food products. When used as a fumigant, the halogen, e.g., bromine, of the halophor vaporizes from the halophor, thereby permeating the food products and killing the insects with which it comes into contact.

In accordance with one embodiment of the present invention, there is contemplated a composition comprising a free-flowing, particulate, inert, amorphous siliceous carrier having a biocidal amount of the halophor compositions of the present invention admixed therewith. The siliceous carrier is water-insoluble and has the halophor, i.e., iodophor or bromophor, adsorbed thereon. The halophor comprises a complex of bromine and/or iodine, halide ion, e.g., alkali or alkaline earth metal halides, e.g., bromides or iodides, and a sulfone, e.g., tetrahydrothiopene-1, 1-dioxide (sulfolane). The halophor prepared with sulfolane exhibits enhanced stability to light.

DETAILED DESCRIPTION OF THE INVENTION

The biocidal compositions contemplated herein comprise a complex of bromine and/or iodine, preferably bromine, alkali metal halide or alkaline earth metal halide, e.g., sodium bromide or calcium bromide, and a sulfone. In a particular embodiment, there is contemplated particulate or granular inert water-insoluble amorphous siliceous carrier containing the aforedescribed complex (halophor). The halophor (bromophor or iodophor) is a liquid at standard conditions of temperature and pressure and, in the aforesaid embodiment, is adsorbed by the siliceous carrier. The aforesaid biocidal compositions may be utilized as germicides, fungicides, insecticides, and for general sanitizing or antiseptic applications. Particularly contemplated herein are halophor, e.g., bromophor, compositions for use as fumigants for fumigation of food commodities and establishments in which food commodities are processed or stored, e.g., enclosures for the storage of grain, or as a soil fumigant for the control of nematodes and rootknot disease.

Halophors contemplated for use herein are prepared by combining the (1) sulfone, (2) bromide, iodide or chloride ion and (3) elemental bromine or iodine. Sulfones that may be employed in preparing the halophors of the present invention include the acyclic sulfones, e.g., dimethyl sulfone, and heterocyclic sulfonanes, e.g., tetrahydrothiophene 1,1-dioxide - both of which will be referred to collectively as sulfones.

The acyclic sulfones may be represented by the graphic formula $R_1-SO_2-R_2$, wherein $R_1$ is a $C_1-C_4$ alkyl group, e.g., methyl, ethyl, propyl and butyl, and $R_2$ is a $C_1-C_4$ alkyl or phenyl group. Typically, $R_1$ and $R_2$ are the same but may be different. Examples of acyclic sulfones include: dimethyl sulfone, diethyl sulfone, di-n-propyl sulfone, dibutyl sulfone, methyl ethyl sulfone and methy phenyl sulfone. Dimethyl sulfone is economically preferred. Acyclic sulfones may be prepared by the oxidation of the corresponding sulfide or sulfoxide at elevated temperatures with an excess of hydrogen peroxide in glacial acetic acid, or with chromic or nitric acid. An alkyl phenyl sulfone may be prepared by reaction of an alkane sulfonic acid with benzene under dehydrating conditions.

The heterocyclic sulfones, i.e., sulfolanes, may be represented by the graphic formula:

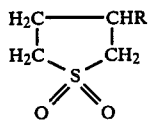

wherein R is hydrogen or a lower alkyl, e.g., $C_1$–$C_4$ alkyl. Sulfolane (tetrahydrothiophene 1,1-dioxide or tetramethylene sulfone) is a commercially available organic solvent. It may be prepared by the addition of sulfur dioxide to 1,3-butadiene at ordinary temperatures, e.g., 25° C. to produce sulfolene, which may be hydrogenated over nickel catalyst to sulfolane. 3-alkyl substituted sulfolanes may be prepared by a corresponding reaction utilizing a 2-alkyl substituted butadiene, e.g., isoprene. In addition to sulfolane, other heterocyclic sulfones that may be used include 3-methyl sulfolane, 3-ethyl sulfolane, 3-n-propyl sulfolane and 3-n-butyl sulfolane.

The halide, i.e., bromide, iodide, or chloride used in the preparation of the bromophor contemplated herein is provided usually by the bromides or iodides of the alkali metals, sodium, lithium or potassium. Alkaline earth metal halides, e.g., the bromides, chlorides or iodides of calcium and magnesium may also be used. Preferably, the aforesaid alkali metal halide is soluble or at least partially soluble in the sulfone. Alternatively, anhydrous hydrogen bromide or hydrogen iodide may be used. The halide may be represented by the formula, MX, wherein M is hydrogen, the alkali or alkaline earth metals, and X is iodine, bromine, or chlorine, e.g., MBr, MI, or MCl.

The amount of halide used with the sulfone can vary. In general, the mole ratio of the halide ion to halogen, e.g., bromide:bromine ($Br_2$), may vary from 1:1 to 1:12, more usually from 1:1 to 1:3. Preferably, the mole ratio is about 1:2. Basis the halide (bromide, chloride or iodide) ion and halogen (bromine or iodine) used, the halophor (bromophor or iodophor) may contain one or more of the following halide or interhalide species: $BR^{-}_3$ and $BR_2$ multiples thereof, e.g., $Br^{-}_5$, $Br^{-}_7$, $Br^{-}_9$ etc; $Br_2I^{-}$ and $Br_2$ multiples thereof, e.g., $Br_4I^{-}$; $BrI^{-}_2$ and $Br_2$ or $I_2$ multiples thereof, e.g., $Br_3I^{-}_2$, $Br_5I^{-}_2$, $BrI^{-}_4$ and $BrI^{-}_6$ etc; and $I^{-}_7$ and $I_2$ multiples thereof, e.g., $I^{-}_5$, $I^{-}_7$, etc., $Br_2Cl^{-}$ and $Br_2$ multiples thereof; and $I_2Cl^{-}$ and $I_2$ multiples thereof.

The amount of halogen, e.g., bromine, complexed with the sulfone-halide mixture may vary. Usually the amount of halogen present in the halophor as elemental halogen, e.g., $Br_2$ or $I_2$, will vary from about 10 to about 50, e.g., 25 to 40, weight percent.

In accordance with a preferred embodiment of the present invention, the metal halide is first admixed with or preferably dissolved in the sulfone and halogen, i.e., bromine and/or iodine, introduced into the mixture or solution. While not wishing to be bound by any theory, it is believed that halogen so introduced reacts with the metal halide to form polyhalo species rather than reacting with the sulfone, thereby providing a product which yields significant quantities of available halogen, e.g., bromine, for those applications, e.g., biocidal applications, requiring same. In a preferred embodiment, the sulfone, e.g., sulfolane, and halide, e.g., sodium, potassium or lithium bromide, are substantially free of water. Most preferably, the system is substantially free of water, i.e., not more than about 5 weight percent water, which it is believed leads to enhanced stability of the halophor prepared in accordance with the present process.

Halophors described herein can be readily produced by combining the sulfone metal halide, and bromine (and/or iodine) under suitable complexing conditions. For bromophors, it is preferred that liquid bromine be combined with a mixture, e.g., solution, of the sulfone and metal bromide, e.g., sodium bromide, lithium bromide or potassium bromide. The reaction between liquid bromine and the sulfone-halide liquid mixture is generally highly exothermic and hence the reaction mixture should be vigorously stirred and cooled if necessary as the bromine is added slowly. It is generally advisable to maintain the temperature of the reaction mixture from about 25° C. to about 55° C., more usually between 40° C. and about 50° C., for best results, although temporary temperature excursions outside such range will yield satisfactory results as long as temperatures at which the halogen reacts irreversibly with the sulfone are avoided for extended periods of time. The reaction between iodine and the sulfone-halide mixture is generally less exothermic than when bromine is used; however, the same precautions and temperatures may be used to prepare the iodophors as are used to prepare the bromophors. Temporary temperature excursions outside the aforedescribed range will yield satisfactory results as long as temperatures at which the halogen reacts irreversibly with the sulfone are avoided for extended periods of time.

In addition, stabilizers, such as acids that are stable under the conditions of use, may be added to the halophor. Some acids that have been suggested for use as stabilizers for halophors, e.g., bromophors, are hydrochloric acid, hydrobromic acid, phosphoric acid, and acetic acid.

The halophor may, in accordance with a preferred embodiment of the present invention, be admixed with a siliceous carrier to provide a composition having sufficient halophor to provide at least a biocidal, e.g., insecticidal, amount of the halophor, e.g., bromophor. A biocidal amount is that amount of halophor that is sufficient to liberate a toxic dosage of elemental bromine and/or iodine, i.e., a dosage sufficient to kill at least 99 percent of the biologic population exposed thereto. Typically, an insecticidal amount is a dosage that results in the killing of at least 99 percent of the biologic population, i.e., the insect population, after their exposure for 24 hours at ambient pressure and a temperature of 25° C. to the halogen(s) liberated from the halophor.

The siliceous carrier for the halophor is an inert particulate amorphous siliceous material which is free-flowing and water-insoluble, i.e., has a water solubility at 20° C. of less than 0.5 grams per liter. The siliceous material is chemically inert with respect to the halophor admixed therewith, e.g., the siliceous carrier does not react chemically with the halophor.

The particulate siliceous carrier is of such size as is suitable for the intended use of the herein described halophor composition as a biocidal agent. The particles, for practical purposes, are generally in the range of from 10 to 400 mesh (U.S. Standard Screen), i.e., in the size range of between -10 and +400 mesh, usually -12 or -14, +325 mesh. The siliceous carrier will typically have an oil absorption of between about 75 and 350 milliliters of dibutyl phthalate per 100 grams of silica. Oil absorption values can be obtained using a method like that described in ASTM D2414-65. For most applications, the oil absorption of the siliceous carrier will be between about 150 and 300 milliliters/100 grams.

The siliceous carrier can be a synthetic amorphous silica or naturally occurring silica- or silicate-containing minerals. Exemplary of synthetic amorphous silicas that may be used as the carrier are precipitated silicas, fumed silicas and silica gels, including hydrogels and xerogels. The aforesaid subcategories of synthetic amorphous silicas refer generally to the method of their preparation. Precipitated silicas are prepared by mixing an alkali metal silicate, e.g., sodium silicate, and a mineral acid, e.g., hydrochloric acid, sulfuric acid or carbonic acid, to cause precipitation of very fine silica particles which are washed free of residual alkali metal salts and dried. Precipitated silicas may be prepared by the methods described in U.S. Pat. No. 2,940,830. Fumed silicas are generally prepared by the flame-hydrolysis of silicon tetrachloride to form a fine silica and by-product hydrochloric acid. Silica gel may be prepared by mixing an alkali metal silicate, e.g., sodium silicate, with a mineral acid at a pH and silica concentration such that a gelatinous precipitate (hydrogel) is formed. The hydrogel can then be washed to remove electrolytes either before or after drying, e.g., spray drying. When the hydrogel is dehydrated, a xerogel is formed. This is accomplished by replacing the hydrogel water prior to the drying step with a readily volatile material, e.g., an alcohol.

Precipitated silica particularly useful as a carrier for the halophor described herein is material having a BET surface area of between about 130 and about 180 square meters per gram, an oil absorption of between 200 and 270, e.g., between about 230 and 260, milliliters of dibutyl phthalate per 100 grams of silica, a water absorption of between about 160 and 180 milliliters per 100 grams of silica, a median agglomerate particle size of between about 6 and 15, preferably between 8 and 12, microns (micrometers), as measured by a Coulter counter, and a specific volume of at least 3.5 cubic centimeters per gram, e.g., 3.5–4.7 cm$^3$/g, when compacted with an applied pressure of 17 pounds per square inch (psi) (117 kPa).

Such particularly useful precipitated silica may be prepared by (a) establishing an alkali metal silicate, e.g., sodium silicate, aqueous solution having an alkali metal oxide concentration of from about 5.6 to 7.2 grams per liter and a temperature of between about 190° F. (88° C.) and 198° F. (92° C.), (b) slowly adding from 2 to 5 times the original amount of alkali metal silicate to the aqueous solution while simultaneously acidifying the aqueous solution at a rate to maintain the alkali metal oxide concentration therein substantially constant, (c) adding further acidifying agent to the resulting slurry until the pH is from 8 to 9, (d) ageing the slurry at between 188° F. (87° C.) and about 198° F. (92° C.) for from 15 to 90 minutes, (e) adding additional acidifying agent to the aged slurry until the pH is from 4.0 to 4.7 and (f) separating (from the slurry), washing and drying the silica product.

Also contemplated for use as the siliceous carrier are naturally occuring silica- or silicate-containing minerals. These materials are rich in hydrated silicates of aluminum or magnesium and include such clays as montmorillonite, attapulgite, kaolinite, talc, bentonite, and Fuller's earth, diatomaceous earth, naturally occurring amorphous aluminum silicate (zeolites) and the synthetic zeolites which are an amorphous combination of precipitated alumina and silica. Also contemplated for use as a carrier herein are precipitated calcium silicates, which include synthetic silicas containing small amounts, e.g., 1 to 10 percent, of calcium, calculated as calcium oxide. The above-described synthetic siliceous materials are generally commercially available or can be prepared by techniques known in the art.

The particulate halophor compositions of the present invention can be readily produced by admixing at least one siliceous carrier with the halophor, e.g., bromophor, under conditions designed to obtain a homogeneous mixture. The liquid halophor can be applied to the particulate siliceous carrier by spraying, preferably while the siliceous carrier is stirred or tumbled, to achieve uniform distribution of the halophor on the carrier. Alternatively, the liquid halophor can be poured onto the granular carrier and the mixture thereafter stirred. Generally, it is preferred to maintain the halophor at temperatures of 55° C. or less to prevent irreversible reaction of the halogen, e.g., bromine, with the sulfone.

The amount of bromophor or iodophor admixed with the siliceous carrier may vary widely and may be up to that amount which causes the carrier to lose its free-flowing property, i.e., up to the maximum adsorptivity of the siliceous carrier utilized. Hence, the maximum amount of halophor that can be sorbed by the siliceous carrier will be a function of the adsorbtivity of the carrier. A measure of a siliceous carrier's adsorbtivity is its oil absorption. The higher the oil absorption value for a particular siliceous carrier - the greater is the amount of halophor that can be retained by the carrier and still remain freeflowing.

The amount of halophor, e.g., bromophor or iodophor, sorbed onto the siliceous carrier is advisedly selected to provide a free-flowing, granular halophor composition containing at least a biocidal amount of available bromine and/or iodine (or bromiodide). Since the amount of iodine or bromine required for biocidal activity will vary with the end use, e.g., fumigant, sanitizer, or disinfectant, the quantity of halophor sorbed onto the carrier may likewise vary and will also depend on the amount of halogen, i.e., bromine and/or iodine present in the halophor available for the particular biocidal application.

It is contemplated that the siliceous carrier, depending on its adsorbtivity, may contain from about 1 to about 80 weight percent of the halophor, basis the weight of the siliceous carrier, e.g., between about 5 and 75 or 10 and 40, weight percent of halophor. For some applications between about 1 and 35 parts by weight of halophor per 100 parts by weight of the siliceous carrier may be sufficient to provide the biocidal, e.g., the insecticidal, amount of available bromine or iodine.

It is contemplated that more than one amorphous, siliceous carrier maybe used to prepare the particulate halophor compositions of the present invention. Thus mixtures of siliceous carriers may be used. It is further contemplated that particulate halophor compositions containing high levels of halophor (in the form of a masterbatch) may be prepared with highly abosrptive siliceous carrier(s) and subsequently diluted with other chemically inert solid diluents, e.g., less absorptive (and perhaps less costly) siliceous carriers, clays, and inorganic, preferably water soluble salts. Such particulate halophor masterbatch compositions may contain from about 30 to about 80, e.g., 50 to 75, weight percent halophor. Inorganic salts contemplated are alkali metal sulfates, phosphates, (orthophosphates and polyphosphates) carbonates and chlorides. The salts of sodium and potassium are preferred for most applications. Preferably, the salts are used in their anhydrous form.

The compositions of the present invention are more particularly described in the following Examples which are intended as illustrative only since numerous modifications and variations therein will be apparent to those skilled in the art.

EXAMPLE 1

A reaction flask was charged with 84.0 grams (0.7 mole) of sulfolane and 16.0 grams (0.18 mole) of lithium bromide. The mixture was heated to 100° C. with stirring to facilitate dissolution of the lithium bromide in the sulfolane and then cooled to 45° C. Liquid bromine (61.3 grams, 19.8 milliliters, 0.38 mole) was added slowly and with stirring to the mixture in the reaction flask over thirty minutes while maintaining the reaction mixture in the temperature range of 40° C.-45° C. The reaction product comprised 52.1 weight percent sulfolane, 9.9 weight percent lithium bromide and 38.0 weight percent bromine (Br$_2$). The reaction product was cooled to 30° C., transferred to a glass bottle and stored at a constant temperature of 30° C. Periodically, a sample was removed from the bottle and tested by thiosulfate titration for the amount of available bromine remaining in the stored reaction product. Results are tabulated in Table I.

TABLE I

| Time, Wks. | Wt. % Available Bromine | Time, Wks. | Wt. % Available Bromine |
|---|---|---|---|
| Start | 35.8 | 4 | 34.0 |
| 3 Days | 35.5 | 5 | 33.6 |
| 1 | 35.0 | 6 | 34.8 |
| 2 | 34.6 | 9 | 34.7 |
| 3 | 34.1 | 12 | 34.3 |

EXAMPLE 2

A beaker was charged with 15.0grams of a free-flowing, amorphous, precipitated silica having the following typical physical properties: Surface Area - 260-290 square meters per gram, oil absorption - 260-285 milliliters; pH - 6.5-7.3; median particle size - 28 micrometers; particle size range - 24-34 micrometers. To the beaker was added 30.20 grams of the bromophor of Example I and the mixture stirred and mixed thoroughly to obtain a uniform product. Bromine was observed to vaporize from the product while in the beaker. The silica-bromophor mixture was stored in a glass bottle at a constant temperature of 30° C. Periodically, a sample of the composition was removed and tested by thiosulfate titration for the amount of available bromine remaining in the sample. Results are tabulated in Table II.

TABLE II

| Time, Wks. | Wt. % Available Bromine | Time, Wks. | Wt. % Available Bromine |
|---|---|---|---|
| Start | 21.5 | 2 | 21.4 |
| 3 Days | 20.7 | 4 | 20.4 |
| 1 | 20.8 | 6 | 19.9 |

The date of Table II show that the composition of Example 2 remains relatively stable over the period tested.

Although the present invention has been described with reference to specific details to certain embodiments thereof, it is not intended that such details should be regarded as limitations upon the scope of the invention except as and to the extent that they are included in the accompanying claims.

What is claimed is:

1. A halophor comprising a complex of (a) halogen selected from the group consisting of bromine and iodine, (b) sulfone selected from the group consisting of acyclic sulfones represented by the formula R$_1$—SO$_2$—R$_2$, wherein R$_1$ is a C$_1$-C$_4$ alkyl and R$_2$ is a C$_1$-C$_4$ alkyl or phenyl, and heterocyclic sulfones represented by the graphic formula:

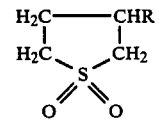

wherein R is hydrogen or C$_1$-C$_4$ alkyl, and (c) halide represented by the formula, MX, wherein M is hydrogen, alkali metal selected from sodium, potassium and lithium, or alkaline earth metal selected from calcium and magnesium, and X is bromine, chlorine or iodine, the mole ratio of halide to halogen being from about 1:1 to 1:12, and the amount of halogen in the complex being between about 10 and about 50 weight percent.

2. The halophor of claim 1 wherein the halogen is bromine and the halide is an alkali metal bromide.

3. The halophor of claim 2 wherein the sulfone is dimethyl sulfone, diethyl sulfone, sulfolane or 3-methyl sulfolane.

4. The halophor of claim 3 wherein the mole ratio of halide to halogen is from about 1:1 to 1:3 and the amount of halogen in the complex is from about 25 to 40 weight percent.

5. The halophor of claim 1 wherein the halide, MX, is a member selected from the group consisting of bromides and iodides of the alkali metals sodium, lithium and potassium.

6. A particulate halophor composition comprising particulate, inert, amorphous siliceous carrier having adsorbed thereon from about 1 to about 80 weight percent of a complex of (a) halogen selected from the group consisting of bromine and iodine, (b) sulfone selected from the group consisting of acyclic sulfones represented by the formula R$_1$—SO$_2$—R$_2$, wherein R$_1$ is a C$_1$-C$_4$ alkyl, and R$_2$ is a C$_1$-C$_4$ alkyl or phenyl, and heterocyclic sulfones represented by the graphic formula:

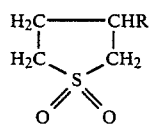

wherein R is hydrogen or $C_1$-$C_4$ alkyl, and (c) halide represented by the formula, MX, wherein M is hydrogen, alkali metal selected from sodium, potassium, and lithium, or alkaline earth metal selected from calcium and magnesium, and X is bromine, chlorine or iodine, the mole ratio of halide to halogen being from about 1:1 to 1:12, and the amount of halogen in the complex being between about 10 and about 50 weight percent.

7. The halophor composition of claim 6 wherein the sulfone is dimethyl sulfone, diethyl sulfone, sulfolane or 3-methyl sulfolane.

8. The halophor composition of claim 6 wherein the siliceous carrier is a synthetic amorphous silica or naturally occurring silica- or silicate-containing mineral.

9. The halophor composition of claim 8 wherein the siliceous carrier contains from about 5 to about 75 weight percent of the complex.

10. The halophor composition of claim 7 wherein the siliceous carrier is a synthetic amorphous silica or naturally occurring silica- or silicate-containing mineral.

11. The halophor composition of claim 10 wherein the halogen is bromine, and the halide is sodium bromide, potassium bormide, lithium bromide, calcium bromide or magnesium bromide.

12. The halophor composition of claim 11 wherein the mole ratio of halide to halogen is from about 1:1 to 1:3 and the amount of halogen in the complex is from about 25 to 40 weight percent.

13. The halophor composition of claim 12 wherein the siliceous carrier is precipitated amorphous silica and the sulfone is sulfolane.

14. The halophor composition of claim 11 wherein the bromide is sodium bromide, lithium bromide or potassium bromide.

15. The halophor composition of claim 13 wherein the bromide is lithium bromide, sodium bromide or potassium bromide.

16. A fumigant comprising particulate, inert amorphous siliceous carrier having adsorbed thereon an insecticidal amount of a bromophor complex of (a) bromine, (b) sulfone selected from the group consisting of acyclic sulfones represented by the formula $R_1$—$SO_2$—$R_2$, wherein $R_1$ is a $C_1$-$C_4$ alkyl, and $R_2$ is a $C_1$-$C_4$ alkyl or phenyl, and heterocyclic sulfones represented by the graphic formula:

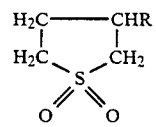

wherein R is hydrogen or $C_1$-$C_4$ alkyl, and (c) bromide represented by the formula, MBr, wherein M is hydrogen, alkali metal selected from sodium, potassium and lithium, or alkaline earth metal selected from calcium and magnesium, the mole ratio of bromide to bromine being from about 1:1 to 1:12, and the amount of bromine in the complex being between about 10 and 50 weight percent.

17. The fumigant of claim 16 wherein the sulfone is dimethyl sulfone, diethyl sulfone, sulfolane or 3-methyl sulfolane.

18. The fumigant of claim 17 wherein from about 10 to about 40 weight percent of the siliceous carrier-bromophor complex composition is the bromophor complex.

19. The fumigant of claim 18 wherein the bromide is alkali metal bromide selected from lithium bromide, sodium bromide, and potassium bormide, the sulfone is sulfolane, and the mole ratio of bromide to bromine in the complex is between about 1:1 and 1:3.

20. The fumigant of claim 19 wherein the siliceous carrier is precipitated, amorphous silica.

21. A method for preparing a halophor of a complex of (a) halogen selected from the group consisting of bromine and iodine, (b) acyclic sulfone represented by the formula $R_1$—$SO_2$—$R_2$, wherein $R_1$ is a $C_1$-$C_4$ alkyl, and $R_2$ is a $C_1$-$C_4$ alkyl or phenyl, or heterocyclic sulfone represented by the graphic formula:

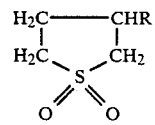

wherein R is hydrogen or $C_1$-$C_4$ alkyl, and (c) halide represented by the formula, MX, wherein M is hydrogen, alkali metal selected from sodium, potassium and lithium, or alkaline earth metal selected from calcium and magnesium, and X is bromine, chlorine or iodine, comprising admixing the sulfone and halide and thereafter introducing halogen into the sulfone-halide admixture in amounts sufficient to provide between about 10 and about 50 weight percent halogen in the halophor complex, the mole ratio of halide to halogen being from about 1:1 to 1:12.

22. The method of claim 21 wherein the halide is dissolved in the sulfone prior to introducing the halogen.

23. The method of claim 21 wherein the temperature at which the halophor complex is prepared is from about 25° C. to about 55° C.

24. The method of claim 23 wherein the halogen is bromine, the halide is lithium bromide, sodium bromide or potassium bormide, and the sulfone is sulfolane.

25. The method of claim 24 wherein the halophor is prepared in the substantial absence of water.

* * * * *

UNITED STATES PATENT AND TRADEMARK OFFICE
CERTIFICATE OF CORRECTION

PATENT NO. : 4,844,899

DATED : July 4, 1989

INVENTOR(S) : Robert H. Juda, et al

It is certified that error appears in the above-identified patent and that said Letters Patent is hereby corrected as shown below:

Column 8, line 23, at the end of the line "SO" should be --$SO_2$--.

line 24, delete "2".

Claim 11, column 9, line 37, "bormide" should be --bromide--.

Signed and Sealed this

Twenty-sixth Day of May, 1992

Attest:

DOUGLAS B. COMER

*Attesting Officer*    Acting Commissioner of Patents and Trademarks